United States Patent [19]
Dean et al.

[11] Patent Number: 5,531,229
[45] Date of Patent: Jul. 2, 1996

[54] BODY PART IMMOBILIZATION DEVICE

[76] Inventors: Richard D. Dean, 21617 W. 71st Ter., Shawnee, Kans. 66218; Dick A. Jones, 8112 Lichtenauer Dr., Shawnee, Kans. 66219

[21] Appl. No.: 375,655

[22] Filed: Jan. 20, 1995

[51] Int. Cl.$^6$ .............................. A61F 5/00; A61F 11/00; H05G 1/02
[52] U.S. Cl. .......................... 128/866; 606/130; 602/17; 602/7; 128/845; 128/857; 5/637; 378/195
[58] Field of Search .................... 602/5–7, 17; 128/866, 128/857, 861, 862, 845, 870–871, 653.1, 653.2, 653.5; 606/130; 5/621, 622, 636, 637; 378/195, 204, 205, 208

[56] References Cited

U.S. PATENT DOCUMENTS

| | | | |
|---|---|---|---|
| 4,256,112 | 3/1981 | Kopf et al. | 606/130 |
| 4,400,820 | 8/1983 | O'Dell et al. | 128/845 X |
| 5,081,665 | 1/1992 | Kostich | 602/17 X |
| 5,207,688 | 5/1993 | Carol | 606/130 |
| 5,207,716 | 5/1993 | McReynolds et al. | 128/870 |
| 5,334,133 | 8/1994 | Carroll | 128/870 X |
| 5,370,117 | 12/1994 | McLaurin, Jr. | 128/845 X |

OTHER PUBLICATIONS

Med Tec, Inc. advertisement, MT#47 3000; Jul. 1993.
Positech, Inc. advertisement re radiolucent bite block head stabilizer.
Raycast HP advertisement re radiotherapy immobilization system from nuclear associates.

*Primary Examiner*—Linda C. Dvorak
*Attorney, Agent, or Firm*—Hovey, Williams, Timmons & Collins

[57] ABSTRACT

An improved immobilization device (10) for specific patients and body parts is provided which insures that a body part is immobilized and can be successively repositioned in the same location during successive treatments. The device (10) is thus particularly applicable for treatment such as radiation therapy where it is important to properly focus treating radiation on a particular locale from treatment-to-treatment. The device (10) preferably includes a frame assembly (16) adapted to rest upon a surface and which supports a preformed, shape-retaining material (12) presenting a concavity (14) substantially conforming with a selected body part to be immobilized. The device (10) when used for head immobilization, may also be provided with stabilizer (98) in the form of an adjustably positioned bite block (134). Hold-down straps (52, 54) can also be employed for further immobilization. Additional immobilization may also be provided by a nose bridge holddown assembly (136) operably coupled to frame assembly (16) and engaging nose bridge and eyebrow region of the patient.

12 Claims, 4 Drawing Sheets

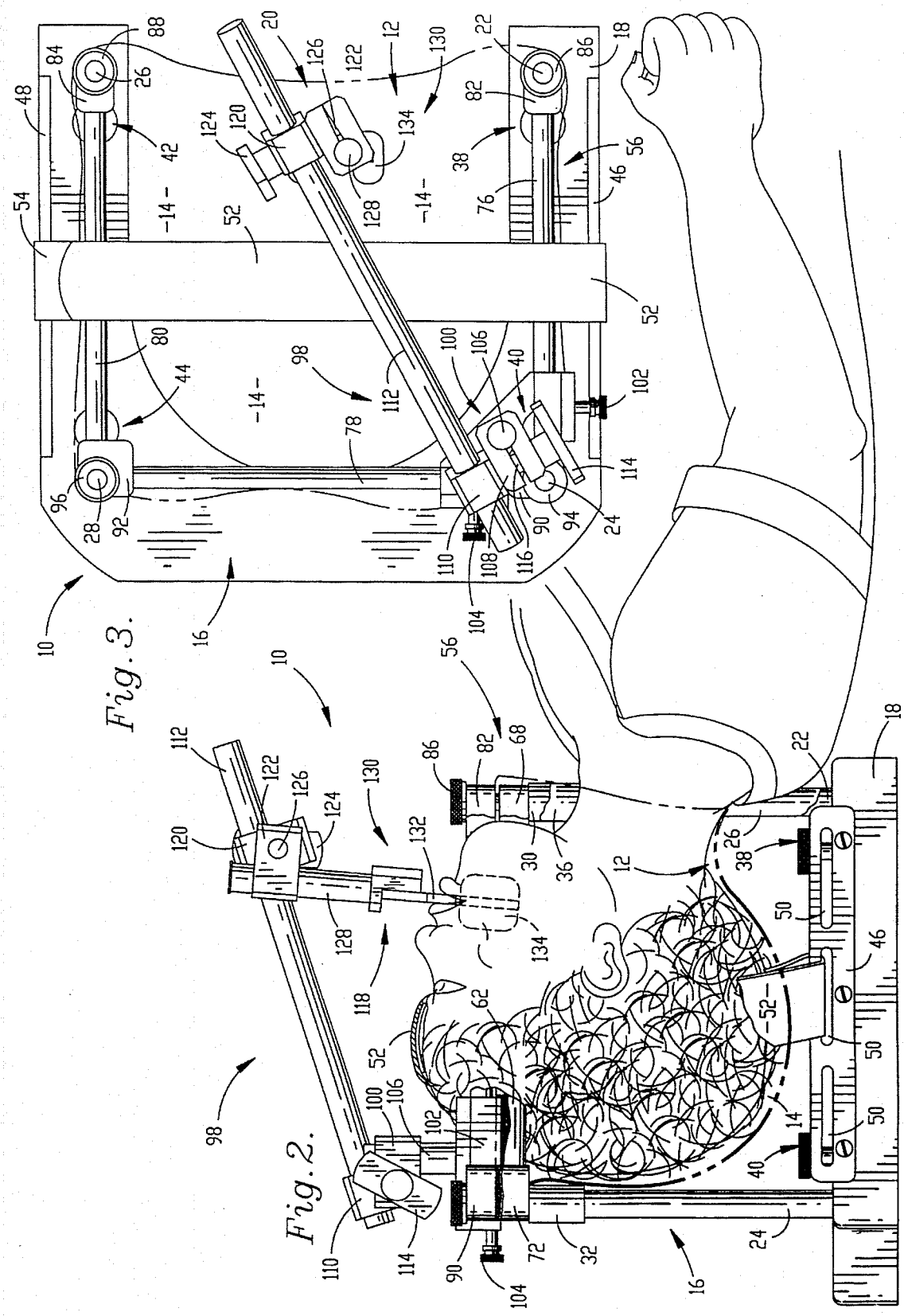

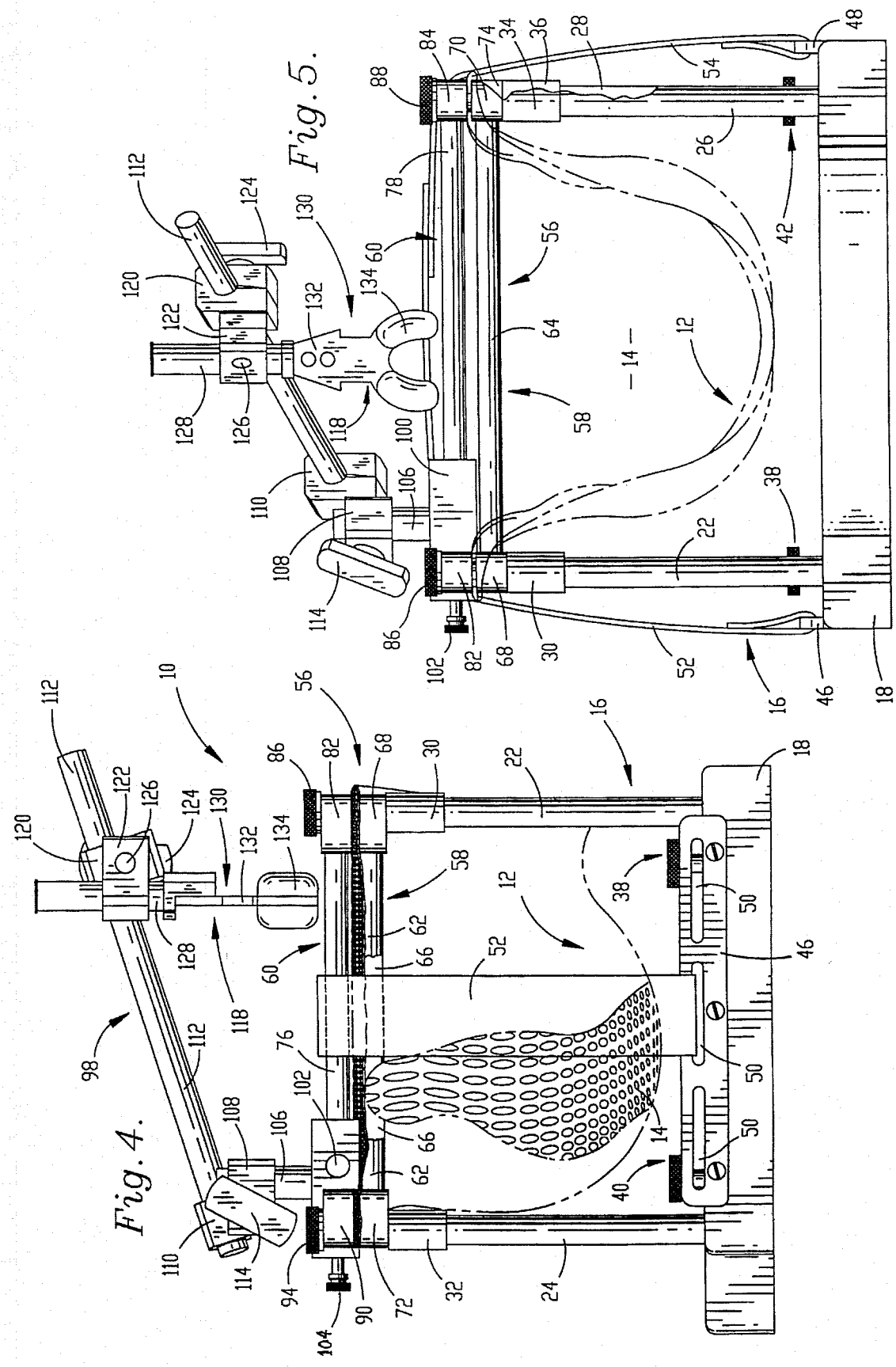

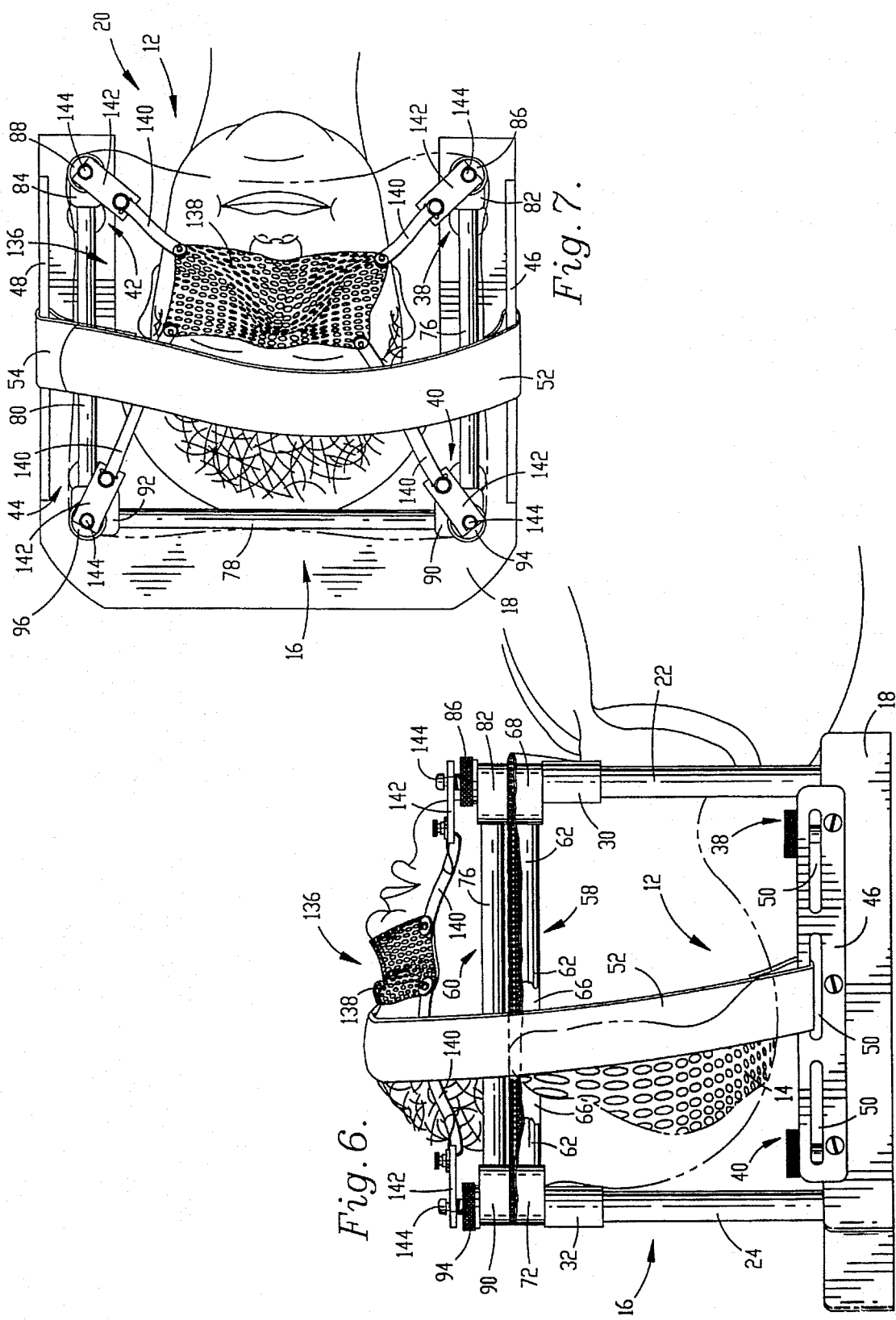

BODY PART IMMOBILIZATION DEVICE

BACKGROUND OF THE INVENTION

1. Field of the Invention

The present invention is broadly concerned with a device for immobilizing body parts in order to permit more effective and repeatable medical treatments. More particularly, the invention pertains to an immobilizing device designed to substantially completely immobilize a body part such as a patient's head, while facilitating repeatability of placement of the body part so that successive treatments can be most effectively carried out. The devices of the invention greatly facilitate radiation treatment commonly prescribed for patients suffering from internal tumors.

2. Description of the Prior Art

There is frequently a need to immobilize body parts of patients undergoing medical treatment. To give but one example, patients suffering from brain tumors require repeated doses of radiation. A common problem with such patients is the need to repeatably position the patient's head in an identical location, so that radiation can be applied only to the area of the internal tumor. A related difficulty is the need for fully immobilizing the patient's head during the treatments.

A number of immobilization devices have been proposed in the past. For example, it is known to provide an essentially flat, U-shaped frame member having a stretch of perforate polycaprolactone mesh material secured therein. In initial fitting of this unit, the mesh material is warmed and stretched over the patient's face in a conforming relationship. The mesh material then quickly hardens as a shape-retaining three-dimensional pattern conforming with the patient's face. During subsequent radiation treatments, the patient is placed in a supine position on a table, and the preformed unit is placed over the patient's face in an attempt to hold the patient's head immobilized. In other alternatives, the patient may be positioned in a prone or tilted position, in accordance with the dictates of treatment and the initial fitting of the mesh material.

Another type of immobilization device includes an upstanding pedestal adapted to be mounted upon a support surface. The upper end of the pedestal carries an adjustable arm member which in turn supports a bite block which fits within the patient's mouth and is grasped by the patient's teeth.

Despite the widespread use of prior immobilization devices, there remains an unsatisfied need in the art for a truly effective way of both immobilizing a patient's body part and insuring repeatability of placement of the body part for successive medical treatments.

SUMMARY OF THE INVENTION

The present invention overcomes the problems outlined above, and provides a greatly improved body part immobilization device. Broadly speaking, the device of the invention includes a section of preformed, shape-retaining material which presents a concavity substantially conforming with a selected body part to be immobilized and is configured for receiving and holding the body part. The overall device further includes a frame assembly adapted to rest upon a support surface and operably coupled with the preformed section for holding the concavity, and thus the patient's body part, in an elevated position above the support surface. In this fashion, the body part-receiving preformed section is placed in tension to enhance the rigidity of the device in use. At the same time, the preformed nature of the section insures essentially constant placement of the body part treatment-to-treatment.

In one embodiment of the invention, a head immobilizing device is provided. In this form of the invention, the frame advantageously includes a generally U-shaped base with upstanding support legs secured thereto; means is mounted on the upper end of the support legs for holding marginal regions of the preformed section, with the latter extending downwardly from the marginal regions to define the body part-receiving concavity. In addition, stabilizing means is also preferably provided which is supported on the frame assembly and includes structure such as a bite block adapted to be taken into the mouth of the patient. Finally, strap means coupled with the frame assembly can also be provided, which are oriented to extend over and engage the forehead of the patient during use of the head immobilization device.

BRIEF DESCRIPTION OF THE DRAWINGS

FIG. 2 is a view similar to that of FIG. 1, but with parts broken away to further depict the construction and use of the immobilization device;

FIG. 3 is a plan view of the device illustrated in FIGS. 1 and 2;

FIG. 4 is a side view of the device illustrated in FIG. 1, when not in use;

FIG. 5 is an end view of the device depicted in FIG. 4, viewing the open entrance end of the device;

FIG. 6 is a side view similar to that of FIG. 1, but depicting another embodiment of the invention making use of a nose bridge holddown device; and FIG. 7 is a plan view of the apparatus depicted in FIG. 6.

DETAILED DESCRIPTION OF THE PREFERRED EMBODIMENTS

Figure 1:
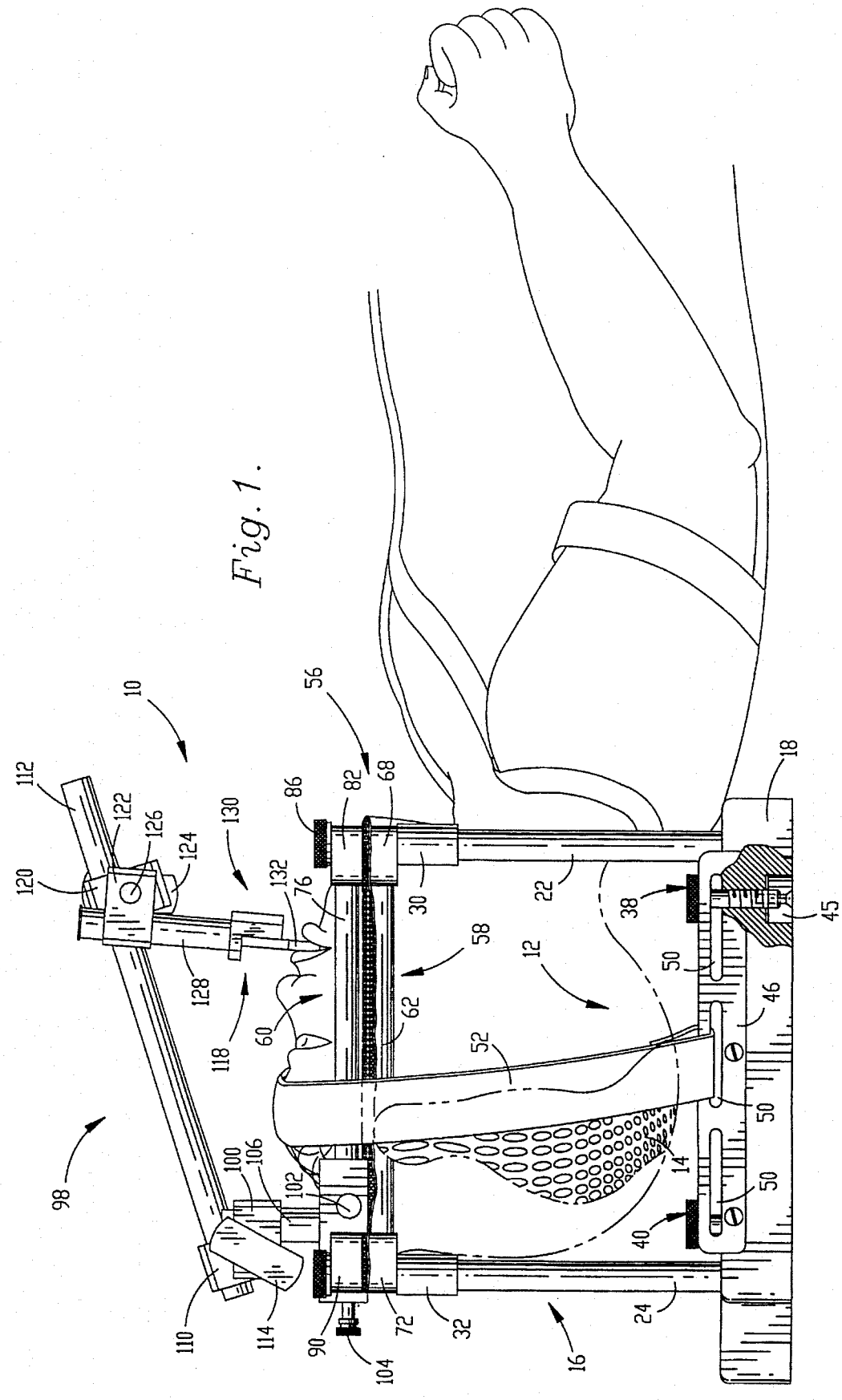
FIG. 1 is a side view of a preferred head immobilization device in accordance with the invention shown during use thereof with a patient's head immobilized.

Referring now to the drawings, and particularly FIGS. 3–5, a head immobilization device 10 is illustrated. Broadly speaking, the device 10 includes a section 12 of preformed, shape-retaining mesh material presenting an upwardly opening concavity 14; the latter substantially conforms with the head of a particular patient and is configured for receiving and holding that patient's head. In addition, the device 10 includes a frame assembly broadly referred to by the numeral 16 which supports and holds the section 12 with the concavity 14 in an elevated position.

In more detail, the section 12 is advantageously formed from an initially flat sheet of mesh-type thermoplastic polycaprolactone material characterized by the property of being readily moldable upon moderate warming, but which becomes substantially shape-retaining thereafter. Such material is commercially available from the WFR/Aquaplast Corporation of Wyckoff, N.J. As depicted, the material is perforated ⅛" Aquaplast of orthopaedic grade. This material generally has a yield stress of about 16–17 MPa, a maximum stress of around 42–45 MPa and a percent elongation at break of from about 960–980. It will be understood, however, that while the Aquaplast material is preferred, the invention is not so limited.

The frame assembly 16 includes a generally U-shaped base 18 (see FIG. 3) presenting an open end 20. The base 18 supports a total of four upstanding, spaced apart, corner-mounted support legs 22, 24, 26, 28. Each of the legs 22–28 includes, at its uppermost end, a corresponding tubular socket 30, 32, 34, 36 presenting an apertured upper end. Additionally, four base leveling assemblies 38, 40, 42, 44 are provided adjacent the lower end of each of the legs 22–28. The assemblies 38–44 permit manual, up and down adjustment of leveling pads 45 (see FIG. 1) at the lower surface of base 18. A pair of slotted strap mount bars 46, 48 are respectively secured to the outer edge of each laterally spaced apart leg of base 18. As best shown in FIG. 4, the bars 46–48 are provided with mounting slots 50 permitting attachment of stabilizing straps 52, 54, the use of which will be described hereinafter.

The overall frame assembly 16 further includes an upper frame member 56 adapted to hold the upper margins of preformed section 12. In particular, the member 56 is of substantially U-shaped configuration and includes a lower U-frame 58 as well as a mating upper U-frame 60. The lower U-frame 58 includes three interconnected rod members 62, 64, 66. Rectangular mounting blocks 68, 70 are secured to the outer ends of rods 62 and 66 and include downwardly extending pins (not shown) adapted to be received within the corresponding tubular sockets 30 and 34 of legs 22 and 26. Each block 68, 70 has an upstanding boss (not shown). A pair of intermediate mounting blocks 72, 74 are provided at the junctures between rods 62 and 64, and rods 64 and 66. The intermediate blocks 72, 74 are likewise provided with downwardly extending pins which are received within the sockets 32 and 36, and upstanding threaded bosses.

The upper U-frame 60 is adapted to mate with lower U-frame 58. To this end, the upper U-frame 60 is formed of three interconnected rods 76, 78, 80. The outer free ends of the rods 76, 80 each have a rectangular, apertured mounting block 82, 84 which are adapted to receive the corresponding bosses. Knurled nuts 86, 88 are provided for interconnecting the free ends of the upper and lower U-frames 58, 60. Intermediate apertured mounting blocks 90, 92 are located at the juncture between rods 76, 78 and 78, 80 and receive corresponding bosses. Again, knurled nuts 94, 96 are employed to interconnect the upper and lower U-frames.

As best seen in FIGS. 4 and 5, the upper margins of section 12 of perforate material are sandwiched between the U-frames 58 and 60, with the upwardly extending bosses 71 and 75 extending through adjacent perforations thereof. Tightening of the nuts 86, 88, 94, 96 serves to firmly clamp the upper marginal portions of the section 12 within upper frame 56. At the same time, the upper frame assembly 56 is firmly seated within and supported by the upstanding legs 22–28.

The overall device 10 is further provided with additional stabilizing means 98. The latter comprises a corner fixture 100 having orthogonal, downwardly opening slots therein adapted to seat upon the portions of rods 76, 78 adjacent intermediate block 90. Set screws 102, 104 are used to secure fixture 100 in place. A central post 106 extends upwardly from fixture 100 and supports a pair of adjacent, generally U-shaped clamp blocks 108, 110. As best seen in FIG. 3, the clamp block 108 is disposed about post 106, whereas clamp block 110 surrounds and supports an elongated support rod 112 which extends over concavity 14. A rotatable clamp block tightener 114 including transverse connecting rod 116 is operatively coupled with the clamp blocks 108, 110, for the purpose of selectively tightening and loosening the blocks about post 106 and support rod 112. In addition, rod 116 permits selective up and down pivotal adjustment of rod 112 about the axis of the rod 116. Hence, the rod 112 may be raised or lowered and tightened in place in any one of a number of selected angular positions. Side-to-side adjustment of the rod 112 is likewise afforded by post 106 and block 108. Thus, the rod 112 may be selectively adjusted side-to-side and vertically over concavity 14.

A bite block assembly 118 is secured to rod 112 adjacent the outer end thereof. In particular, the assembly 118 includes a pair of adjacent clamp blocks 120, 122, which are selectively tightenable by means of tightener 124 including connecting rod 126. As illustrated in FIG. 3, the clamp block 120 is disposed about rod 112, whereas clamp block 122 supports a vertically extending post 128. Referring to FIG. 4, it will be observed that a bite block 130 is affixed to the lower end of post 128. The bite block 130 is itself conventional, and includes plate 132 and lowermost mouth piece 134. The clamp blocks 120, 122 allow adjustment of the assembly 118 relative to rod 112. That is, the entire assembly 118 may be rotated about the axis of rod 112, and alternately, the bite block assembly 130 may be rotated about the axis of post 128. Again, the assembly 118 can be selectively tightened into any one of a number selected positions using tightener 124. It will be appreciated that once the knobs 114 and 124 are tightened, the bite block assembly will remain in the desired position for the duration of the patient's treatment. That is, the bite block assembly may be removed by loosening screws 102, 104 without otherwise changing the setting of the assembly; thereafter, it can be replaced by reversing this procedure.

The straps 52, 54 provide yet another means of assisting in head immobilization using device 10. The straps 52, 54 include mating VELCRO (i.e., the well-known flexible hook and eye attachment material) sections in their opposing surfaces, so that the straps can be releasably interconnected. As best shown in FIG. 1, the straps 52, 54 can thus be tightened around the forehead of a patient.

The components making up the frame assembly 16 and stabilizing means 98 are formed of rigid synthetic resin material. Other types of materials could also be used, so long as these components have the necessary structural stability.

In the use of device 10, a section of initially flat perforate material 12 is placed between the upper and lower U-frames 58, 60 to form a subassembly. The material 12 is then heated by dipping in warm water, and while warm is formed around the head of a patient. This is typically done with the patient in a prone or supine position, with the patient's head being pressed downwardly into the warmed, mounted polycaprolactone mesh to form the desired impression. This causes the material 112 to conform to the particular configuration of that patient's head, and thus the preformed material 12 is unique for that particular patient. Upon cooling of the material 12, now in a somewhat stretched condition, the material assumes and maintains its shape conforming to the patient's head.

When the patient needs radiation or other treatment, the preformed material 12, mounted with the margins thereof between the U-frames 58, 60, is placed on frame assembly 16. Specifically, the depending pins provided on blocks 68–74 are inserted within the openings of sockets 30–36 to mount the material 12 subassembly above base 18. The patient, lying in a recumbent position, then places his head within the preformed concavity 14 defined by the material 12. This is illustrated for example in FIGS. 1 and 2. When this occurs, the material 12 is placed in tension, and this serves to provide a significant degree of head immobilization.

In order to provide a still further degree of immobilization, the bite block assembly 118 is used. This involves positioning of rod 112 and assembly 118 over concavity 14 and in a convenient position to allow the patient to take bite block 134 into his or her mouth and grasp the same with the teeth. This is schematically illustrated in FIG. 2. The combination of preformed material 12 and bite block 118 gives a very substantial degree of head immobilization.

Finally, the straps 52, 54 are placed over the patient's forehead and interconnected via the VELCRO surfaces thereof (see FIG. 1). This completes the immobilization of the patient's head, and insures that the radiation or other treatment can be most effectively carried out.

Upon completion of the treatment, the straps 52, 54 are disengaged, and the operator removes bite block 134 by loosening thumb screws 102, 104, allowing the patient to arise from the recumbent position. The frame subassembly defined by U-frames 58 and 60, and the captively retained material 12, can then be removed from frame assembly 16 and stored for reuse with the particular patient.

FIGS. 6–7 illustrate another embodiment of the invention providing alternate or supplemental immobilization. In this case, a nose bridge holddown assembly 136 is employed. The assembly 136 includes a preformed, substantially ridged sheet 138 formed to the contour of the nose bridge and eyebrow areas of the patient, together with four corner straps 140 respectively pivotally secured to the corners of sheet 138. The outer ends of the straps 140 are provided with pivotal connection clips 142 which have apertured outer ends for receiving threaded connectors 144, the latter being threaded into the nuts 86, 88 and 94, 96. The sheet 138 is preferably formed from the same thermoplastic polycaprolactone material used in the formation of section 12. Normally, the assembly 136 would be used in lieu of the bite block assembly 118; however, in certain instances both of these holddown expedients may be employed.

Those skilled in the art will appreciate that the present invention, with appropriate minor modifications, can be used for the immobilization of various body parts, such as limbs or the trunk region of a patient. As such, the invention has wide utility as a patient treatment aid.

We claim:

1. A body part immobilization device, comprising:
    a section of preformed, shape-retaining material presenting a concavity substantially conforming with a selected body part to be immobilized and configured for receiving and holding the selected body part; and
    a frame assembly adapted to rest upon a support surface and operably coupled with said section for holding said concavity in an elevated position above said support surface, said frame assembly including structure for suspension of the body part within said concavity and above said support surface, with said material being placed in tension by the weight of the suspended body part.

2. The device of claim 1, said section being formed of perforate thermoplastic material moldable about the selected body part to present said concavity.

3. The device of claim 2, said material being formed of polycaprolactone.

4. The device of claim 1, said frame assembly presenting a surface-engaging base, a plurality of upstanding support legs secured to said base, and means mounted on the upper ends of said support legs for holding marginal regions of said section, said section extending downwardly from said marginal regions to define said concavity.

5. The device of claim 1, said device being adapted for immobilizing the head of a patient, said frame assembly including a surface-engaging base which is generally U-shaped in configuration.

6. The device of claim 5, including stabilizing means supported on said frame assembly and having structure adapted to be taken into the mouth of said patient and to be grasped by the patient's teeth.

7. The device of claim 6, said stabilizing means comprising an arm operably coupled with said frame assembly and extending to a point above said concavity, said structure being secured to said arm.

8. The device of claim 7, including means for selectively adjusting the position of said arm relative to said frame assembly, and means for adjusting the position of said structure relative to said arm.

9. The device of claim 5, including strap means operably coupled with said frame assembly and adapted to extend over and engage the forehead of said patient.

10. The device of claim 5, including sheet means for engaging the nose bridge and eyebrow region of said patient, and means for securing said sheet means to said frame assembly.

11. The device of claim 1, said material section being custom-formed and fitted to the particular configuration of the selected body part of an individual patient.

12. A head immobilization device, comprising:
    a section of preformed, shape-retaining material presenting a concavity substantially conforming with a head to be immobilized and configured for receiving and holding the head;
    a frame assembly including a generally U-shaped base adapted to rest upon a support surface, said assembly being operably coupled with said section for holding said concavity in an elevated position above said support surface, said frame assembly permitting placement of the head within said concavity; and
    stabilization means supported on said frame assembly and having structure adapted to be taken into the mouth of a patient and to be grasped by the patient's teeth, said stabilizing means comprising an arm operably coupled with said frame assembly and extending to a point above said concavity, said structure being secured to said arm.

* * * * *